United States Patent
O'Brien

(10) Patent No.: US 7,097,861 B1
(45) Date of Patent: Aug. 29, 2006

(54) METHOD OF TREATING LIVESTOCK FOOTBATH SOLUTIONS

(75) Inventor: Michael Christopher O'Brien, Oakdale, CA (US)

(73) Assignee: Jones-Hamilton Co., Newark, CA (US)

( * ) Notice: Subject to any disclaimer, the term of this patent is extended or adjusted under 35 U.S.C. 154(b) by 393 days.

(21) Appl. No.: 10/773,062

(22) Filed: Feb. 5, 2004

Related U.S. Application Data

(60) Provisional application No. 60/445,907, filed on Feb. 7, 2003.

(51) Int. Cl.
*A61K 33/04* (2006.01)
*A61K 33/30* (2006.01)
*A61K 33/34* (2006.01)
*A01N 59/02* (2006.01)
*A01N 59/20* (2006.01)
*A01K 29/00* (2006.01)

(52) U.S. Cl. ............... 424/709; 424/703; 424/637; 424/641; 424/642; 514/887; 422/28; 119/673

(58) Field of Classification Search ........... 424/703, 424/709, 637, 641, 642; 514/887; 422/28; 168/48.1; 119/651, 673; 4/622
See application file for complete search history.

(56) References Cited

U.S. PATENT DOCUMENTS

| | | | |
|---|---|---|---|
| 3,984,540 A * | 10/1976 | Willard, Sr. .............. | 424/116 |
| 5,772,985 A | 6/1998 | Kemp et al. ............... | 424/45 |
| 5,780,064 A | 7/1998 | Meisters et al. ........... | 424/616 |
| 6,162,429 A | 12/2000 | Wallis et al. ............. | 424/93.1 |
| 6,444,707 B1 | 9/2002 | Lampe et al. .............. | 514/642 |

OTHER PUBLICATIONS

Drake, Michael, "Footrot crisis for farmers," Belfast Telegraph, Dec. 26, 2005, p. 1.*
Hauptmeier, Larry D. 'Footrot in Beef Cattle' [online] Iowa Beef Center, Mar. 1997 [retrieved on Apr. 24, 2006], Retrieved from the Internet: <URL: http://www.iowabeefcenter.org/Publications/footrot.pdf>.*
Derwent Abstract 1993-263107 (1993).*
Amers, "Hairy Heel Warts . . . ", Michigan Dairy Review, vol. 1, No. 2, May 1996, pp. 1-3.

* cited by examiner

*Primary Examiner*—John Pak
(74) *Attorney, Agent, or Firm*—MacMillan, Sobanski & Todd, LLC

(57) ABSTRACT

This invention relates to a method of treating a livestock footbath solution comprising adding an alkali metal bisulfate to the solution. The invention also relates to a method of treating a livestock footbath solution comprising adding to the solution a blend of an alkali metal bisulfate and a material to treat a bacterial disease. The invention also relates to a method of treating a livestock footbath solution comprising rotating the addition to the solution of an alkali metal bisulfate and a material to treat a bacterial disease.

16 Claims, No Drawings

METHOD OF TREATING LIVESTOCK FOOTBATH SOLUTIONS

CROSS-REFERENCE TO RELATED APPLICATION

This application claims the benefit of U.S. provisional application Ser. No. 60/445,907, filed Feb. 7, 2003.

BACKGROUND OF THE INVENTION

This invention relates in general to livestock footbaths, and in particular to a method of treating livestock footbath solutions to improve the solutions.

Bacterial diseases of the hoof, such as hairy hoof warts and hoof rot, are common in livestock such as cattle, sheep, goats and horses. These diseases can cause lameness which leads to a decline in animal health and performance as measured by a decrease in body weight and fertility. Animals that are seriously afflicted may need to be culled. Lameness in dairy cattle often causes a significant decrease in milk production. Thus, the bacterial diseases create a financial burden on farmers as well as harming the livestock.

One method to address the disease problem is by the use of a livestock footbath. The footbath holds a solution containing a material to prevent and/or treat the disease, such as an antibiotic or other material such as copper sulfate and/or zinc sulfate. The animal is led to walk through the footbath to immerse the hooves in the treatment solution. For example, dairy cattle are usually led through a footbath on their way to or from the milking parlor.

There are still problems associated with the use of livestock footbaths. Some materials used in footbath solutions are not very effective against the diseases or cause irritation to the hooves of the animals. Another problem is that bacteria-containing organic materials on the hooves of the animals are washed off in the footbath solution. The organic materials build up over time and overcome the ability of the material in the solution to prevent and/or treat the disease. An additional problem is that disposal of the footbath water may raise environmental concerns, as several states are mandating the discontinued use of products containing heavy metals such as copper. Therefore, it would be desirable to provide improved livestock footbath solutions.

SUMMARY OF THE INVENTION

This invention relates to a method of treating a livestock footbath solution comprising adding an alkali metal bisulfate to the solution. In a typical embodiment, the alkali metal bisulfate is sodium bisulfate. Preferably, the addition of the alkali metal bisulfate reduces the pH of the solution to less than about 4. The alkali metal bisulfate is added to the solution at any effective level, preferably between about 10 lbs. and about 35 lbs. of alkali metal bisulfate per 50 gallons of water. Preferably, the alkali metal bisulfate contains less than about 0.01% heavy metals. The alkali metal bisulfate preferably has a Primary Irritation Index of less than about 3.

The invention also relates to a method of treating a livestock footbath solution comprising adding to the solution a blend of an alkali metal bisulfate and a material to treat a bacterial disease. In a typical embodiment, the alkali metal bisulfate is sodium bisulfate, and the material to treat the bacterial disease is copper sulfate and/or zinc sulfate.

The invention also relates to a method of treating a livestock footbath solution comprising rotating the addition to the solution of an alkali metal bisulfate and a material to treat a bacterial disease.

DETAILED DESCRIPTION OF THE INVENTION

The addition of an alkali metal bisulfate to a livestock footbath solution improves the effectiveness of the solution in preventing and/or treating bacterial diseases of the hoof. Any type of alkali metal bisulfate can be added to the solution. Preferably, the alkali metal bisulfate is sodium bisulfate, potassium bisulfate, or a mixture thereof. The sodium bisulfate is a sodium salt of sulfuric acid generally expressed as $NaHSO_4$ (CAS Reg. No. 7681-38-1). It is also known as sodium acid sulfate, sodium hydrogen sulfate, and bisulfate of soda.

One suitable type of sodium bisulfate is the food grade sodium acid sulfate sold by Jones-Hamilton Co., 30354 Tracy Road, Walbridge, Ohio 43465. It has been certified as GRAS (Generally Recognized As Safe), and it meets Food Chemicals Codex, 4th Edition Specifications. The sodium acid sulfate consists of crystalline solid particles having a spherical shape with an average diameter of from about 0.03 mm to about 1 mm, typically about 0.75 mm. The product includes sodium bisulfate in an amount of from about 91.5% to about 97.5% by weight (typically about 93%), and sodium sulfate in an amount of from about 2.5% to about 8.5% by weight (typically about 7%). However, sodium bisulfates that are not food grade can also be used in the invention.

The potassium bisulfate for use in the invention is a potassium salt of sulfuric acid generally expressed as $KHSO_4$ (CAS Reg. No. 7646-93-7). It is also known as potassium acid sulfate and potassium hydrogen sulfate.

The alkali metal bisulfate preferably contains less than about 0.01% heavy metals by weight, and more preferably less than about 0.003%. The low level of heavy metals reduces environmental concerns of disposing of the footbath solution. The Jones-Hamilton sodium acid sulfate is low in impurities, containing less than 0.003% heavy metals as Pb, less than about 0.05% water-insoluble substances, and less than 0.003% selenium.

Preferably, the alkali metal bisulfate is not more than mildly irritating to the hooves and skin of the livestock. The alkali metal bisulfate preferably has a Primary Irritation Index of less than about 3, and more preferably less than about 2. The method for measuring Primary Irritation Index is the well known "Draize grading" method disclosed in the journal article, Draize, J. H., Woodard, G., Calvery, H. O., "Methods for the Study of Irritation and Toxicity of Substances Applied Topically to the Skin and Mucous Membrane", Journal of Pharmacology and Experimental Therapeutics, 1944, Vol. 82, pp. 377–390. The Jones-Hamilton sodium acid sulfate is very mild to the hooves and skin, having a Primary Irritation Index of about 0.

While not intending to be limited by theory, it is believed that the addition of the alkali metal bisulfate to the footbath solution kills bacteria by lowering the pH of the solution. The alkali metal bisulfate is effective for rapidly lowering the pH of the solution, preferably to a pH of less than about 4, and more preferably less than about 3. The alkali metal bisulfate is also effective for keeping the pH low over a prolonged period of usage of the footbath. Preferably, the addition of the alkali metal bisulfate is effective for up to about 400 livestock (e.g., cattle) uses of the footbath to keep the pH of the solution below about 4, usually between about 250 and about 400 livestock uses.

The alkali metal bisulfate can be added to the solution at any effective level. The level added may depend on the pH and/or alkalinity of the water used to make the solution. Typically, the alkali metal bisulfate is added to the solution at a level between about 10 lbs. and about 35 lbs. of alkali metal bisulfate per 50 gallons of water, and frequently at a level between about 15 lbs. and about 25 lbs. of alkali metal bisulfate per 50 gallons of water.

The alkali metal bisulfate kills bacteria in the footbath solution that have built up from the organic material washed off from the livestock's hooves. This results in lower bacterial challenge to the hooves and interdigital skin. The alkali metal bisulfate also kills bacteria on the hooves of the livestock. As a result, the footbath solution is effective for treating bacterial diseases of the hoof.

The alkali metal bisulfate can be used alone in the footbath solution, or it can be used in combination with another material effective to treat a bacterial disease. For example, the alkali metal bisulfate can be used in a blend with copper sulfate or zinc sulfate, or in combination with an antibiotic. Alternatively, the alkali metal bisulfate can be added to the footbath solution in rotation with the other material. For example, the alkali metal bisulfate can be added to the footbath solution every other day, rotating with copper sulfate.

Typically, the livestock footbath solution is composed primarily of water. In addition to the water, alkali metal bisulfate, and optionally another material to treat bacterial disease, the footbath solution can contain any other materials commonly used in footbaths.

In accordance with the provisions of the patent statutes, the principle and mode of operation of this invention have been explained in its preferred embodiments. However, it must be understood that this invention may be practiced otherwise than as specifically explained without departing from its spirit or scope.

What is claimed is:

1. A method of treating livestock hooves for reducing or treating bacterial infections of the hooves comprising:
   providing an aqueous footbath solution comprising 10 to 35 pounds of an alkali metal bisulfate per 50 gallons of water, wherein the pH of the solution is less than about 4; and
   leading a livestock animal to walk through the aqueous footbath solution to immerse the hooves in the solution.

2. A method according to claim 1 wherein the alkali metal bisulfate is sodium bisulfate.

3. A method according to claim 1 wherein the footbath is a cattle footbath.

4. A method according to claim 1, wherein the alkali metal bisulfate kills bacteria in the aqueous footbath solution.

5. A method according to claim 1, wherein the alkali metal bisulfate kills bacteria on the hooves of the livestock.

6. A method according to claim 1, wherein the alkali metal bisulfate reduces the pH of the aqueous footbath solution to less than about 3.

7. A method according to claim 1, wherein the alkali metal bisulfate is effective for between about 250 and about 400 livestock uses of the footbath to keep the pH of the solution at a level less than about 4.

8. A method according to claim 1, wherein the alkali metal bisulfate is present in the aqueous footbath solution at a level between about 15 pounds and about 25 pounds of alkali metal bisulfate per 50 gallons of water.

9. A method according to claim 1, wherein the alkali metal bisulfate contains less than about 0.01 wt % heavy metals.

10. A method according to claim 9, wherein the alkali metal bisulfate contains less than about 0.003 wt % heavy metals.

11. A method of treating livestock hooves for reducing or treating bacterial infections of the hooves comprising:
    providing an aqueous footbath solution comprising 10 to 35 pounds of an alkali metal bisulfate per 50 gallons of water in admixture with an additional agent effective for reducing or treating bacterial infections of the hooves, wherein the pH of the solution is less than about 4; and
    leading a livestock animal to walk through the aqueous footbath solution to immerse the hooves in the solution.

12. A method according to claim 11 wherein the alkali metal bisulfate is sodium bisulfate.

13. A method according to claim 11, wherein said additional agent is copper sulfate and/or zinc sulfate.

14. A method of treating livestock hooves for reducing or treating bacterial infections of the hooves comprising:
    (1) providing a first aqueous footbath solution comprising 10 to 35 pounds of an alkali metal bisulfate per 50 gallons of water, wherein the pH of the solution is less than about 4;
    (2) providing a second aqueous footbath solution comprising an agent effective for reducing or treating bacterial infections of the hooves, wherein said agent is not alkali metal bisulfate; and
    (3) leading a livestock animal to walk through either the first aqueous footbath solution or the second aqueous footbath solution to immerse the hooves in the solution, and then rotating with the other aqueous footbath solution the next time the livestock animal is in need of a footbath treatment.

15. A method according to claim 14 wherein the alkali metal bisulfate is sodium bisulfate.

16. A method according to claim 14, wherein said agent is copper sulfate and/or zinc sulfate.

* * * * *